United States Patent [19]
Guerra

[11] 3,996,923
[45] * Dec. 14, 1976

[54] BLOOD TAKING DEVICE

[76] Inventor: Luis A. Guerra, Apt. 3A, 239 Central Park West, New York, N.Y. 10024

[ * ] Notice: The portion of the term of this patent subsequent to Sept. 23, 1992, has been disclaimed.

[22] Filed: July 24, 1975

[21] Appl. No.: 598,902

Related U.S. Application Data

[63] Continuation-in-part of Ser. No. 344,387, March 23, 1973, Pat. No. 3,906,930.

[52] U.S. Cl. .......................... 128/2 F; 128/DIG. 5; 128/221
[51] Int. Cl.$^2$ .......................................... A61B 5/14
[58] Field of Search ............... 128/2 F, 2 B, 214.4, 128/218 R, 218 D, 218 N, 218 NV, 215, 216, 221, 276, 274

[56] References Cited

UNITED STATES PATENTS

| | | | |
|---|---|---|---|
| 3,143,109 | 8/1964 | Gewertz | 128/276 X |
| 3,181,529 | 5/1965 | Wilburn | 128/DIG. 5 |
| 3,416,567 | 12/1968 | Von Dardel et al. | 128/274 X |
| 3,460,529 | 8/1969 | Leucci | 128/2 F |
| 3,513,829 | 5/1970 | Deuschle et al. | 128/276 X |
| 3,585,996 | 6/1971 | Reynolds et al. | 128/221 X |
| 3,753,432 | 8/1973 | Guerra | 128/DIG. 5 |
| 3,906,930 | 9/1975 | Guerra | 128/2 F |

FOREIGN PATENTS OR APPLICATIONS

| | | | |
|---|---|---|---|
| 1,054,174 | 10/1953 | France | 128/221 |
| 532,192 | 8/1931 | Germany | 128/DIG. 5 |
| 743,839 | 1/1956 | United Kingdom | 128/218 D |

*Primary Examiner*—John D. Yasko
*Attorney, Agent, or Firm*—Blum, Moscovitz, Friedman & Kaplan

[57] ABSTRACT

An improved blood-taking device of the type wherein a hypodermic needle is inserted into a blood vessel and one or more evacuated containers in succession are connected to the needle for collecting blood samples has two valves therein. The first valve closes the proximal end of the needle section when a container is not connected thereto, and the second valve makes it possible to control the difference of pressure utilized for drawing blood from a subject. The second valve can be closed rapidly in the event it is discovered that the needle lies in tissue exterior to a blood vessel rather than in a blood vessel itself, thereby preventing extravasation and hematoma.

10 Claims, 7 Drawing Figures

U.S. Patent    Dec. 14, 1976    3,996,923
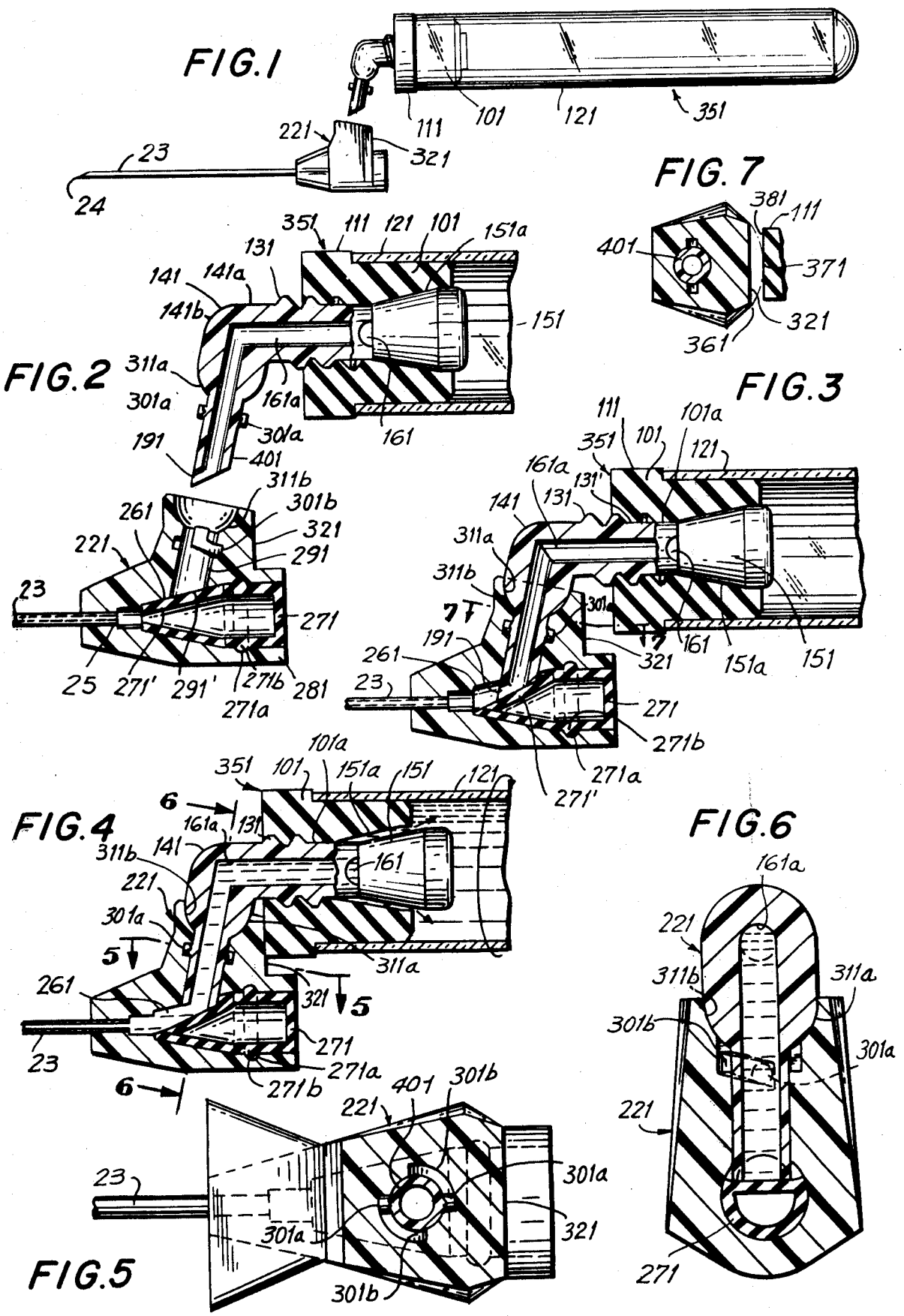

BLOOD TAKING DEVICE

CROSS REFERENCE TO RELATED APPLICATION

The present application is a continuation-in-part application of my co-pending application Ser. No. 344,387 filed Mar. 23, 1973 now U.S. Pat. No. 3,906,930 for IMPROVED BLOOD TAKING DEVICE.

BACKGROUND OF THE INVENTION

It is routine practice in modern hospitals to take blood samples from patients by means of one or more evacuated test tubes placed in succession inside a holder having a two-pointed cannula; one pointed end of the cannula pierces the vein of the patient and the other pointed end pierces the stopper of the evacuated test tube thus providing a flow of blood from the vein to the evacuated tube.

Holders for vacuum tubes are however relatively expensive and therefore non-disposable as well as bulky devices subject to contamination (see U.S. Pat. No. 3,520,292). Also, when double pointed cannulas are not a built-in feature of holders they have to be joined to them by an operator; this process of handling double pointed cannulas is hazardous since the operator may pierce his fingers or contaminate the cannula. Moreover, double pointed cannulas do not easily allow for injection of soluble drugs into the vein, whereas in medical practice it is sometimes desirable to inject drugs by the cannula into the vein after having drawn blood, in this way avoiding the attendant pain of piercing a new vein. Another drawback when using double pointed cannulas is that sometimes blood flushes back from the vein through the cannula to its inner end when withdrawing the tube thus spilling blood over the surroundings. Most important, when using vacuum tubes with a double-ended cannula if the outer tip lodges within tissues rather than a vein, extravasation of blood from the adjacent vein and hematoma may result when the evacuated tube is pierced by the outer tip of the cannula. It is then necessary for the operator to withdraw the cannula as quickly as possible. Even then, the operator may not recognize the situation quickly enough because the full difference in pressure is applied to the outer tip of the cannula as the stopper of the evacuated tube is pierced.

Further, the conventional device has a holder member surrounding the proximal end of the double ended cannula for reception of the stoppered end of the evacuated tube. The diameter of the member is large enough so that the cannula enters the skin at a relatively sharp angle increasing the danger of passing through the further wall of the blood vessel so that the tip of the cannula is within the tissue rather than within the blood vessel. Also, when an evacuated contained is not in position over the proximal end of the cannula clotting at the tip may occur thus interfering with the operation of the device when the taking of an additional specimen is desired.

SUMMARY OF THE INVENTION

A blood-taking device is made in two joinable portions, the first portion including a cannula and a support section, and a second portion including an evacuated container closed by a stopper through which passes an axially and rotatably movable tube. The first and second portions, to be referred to hereinafter as the support and container portions respectively, can be firmly joined together to establish a continuous passage for the flow of blood through the cannula, the support section and the tube into the container. The support section has a first valve therein which is ordinarily closed so that when the tube and container portion are not connected to the support portion, blood in the support section is closed off from contact with the air and possible contamination is avoided. The container portion has a second valve therein which makes it possible to control the difference of pressure applied at the distal tip of the cannula and to cut off the application of vacuum in the event that the cannula is not properly placed in a blood vessel from which blood is to be drawn, thereby avoiding the danger of hematoma. The second valve is operated by rotation of the container around the tube. The distal end of the tube can be seated in the proximal end of the support section to make a continuous passage, the distal end of the tube opening the first valve when the container portion and the support portion are connected. The join between the portions is such that the portions can be separated only when the second valve is tightly closed, thereby protecting the container contents from contamination.

Accordingly, an object of the present invention is to provide an improved blood-taking device having valve means for quickly cutting off the vacuum applied to the tip of a cannula in the event that the cannula is not properly situated in a blood vessel.

Another object of the present invention is to provide an improved blood-taking device with which a plurality of blood specimens can be drawn with a single insertion of a cannula into a blood vessel without incurring the danger of blood clotting in the hiatus between the taking of successive specimens.

An important object of the present invention is to provide an improved blood-taking device in which a blood sample is protected from contamination.

A main object of this invention is to provide a novel stopper for a vacuum container and a novel hypodermic applicator to eliminate the need for a holder as well as double pointed cannulas.

Yet another object of the invention is to provide a hypodermic applicator that allows either to inject soluble drugs into a blood vessel or to draw out blood without spilling due to flush-back.

A significant object of the present invention is to provide an improved blood-taking device in which the operation of said device is free from the danger of causing hematoma.

Yet another object of the present invention is an improved blood-taking device in which the operation of joining the cannula-containing portion to the container portion automatically opens the valve in the support section to provide a continuous and unimpeded channel from the cannula tip to the proximal end of the tube leading into the container.

Still other objects and advantages of the invention will in part be obvious and will in part be apparent from the specification.

The invention accordingly comprises an article of manufacture possessing the features, properties, and the relation of elements which will be exemplified in the article hereinafter described and the scope of the invention will be indicated in the claims.

BRIEF DESCRIPTION OF THE DRAWING

For a fuller understanding of the invention, reference is had to the following description taken in connection with the accompanying drawing, in which:

FIG. 1 is a side view of a device in accordance with the present invention with the cannula-containing portion and the container portion separated;

FIG. 2 is a side view in section of the device in accordance with the present invention with the two portions thereof in position for joining;

FIG. 3 is a side view in section showing the two portions of the device connected together, and with the valve in the container portion closed;

FIG. 4 is a side view similar to that of FIG. 3 but with the valve in the container portion open;

FIG. 5 is a sectional view taken along line 5—5 of FIG. 4;

FIG. 6 is a sectional view along line 6—6 of FIG. 4; and

FIG. 7 is a sectional view along line 7—7 of FIG. 3.

DESCRIPTION OF THE PREFERRED EMBODIMENT

The improved blood-taking device of the present invention consists of two joinable portions, a support portion 221 and a container portion 351 shown separated from each other in FIG. 1. Cannula 23 has a sharp tip 24 for insertion into a blood vessel through the skin of a subject. Proximal end 25 (FIG. 2) of cannula 23 is tightly held in support portion 221 having a passage 261 therethrough. Plug 271 having flexible walls is seated in passage end 281. The flexible wall of plug 271 lies across opening 291' of aperture, i.e., socket 291, so that plug 271 seals opening 291' and passage end 281 simultaneously.

Aperture 291 is fitted with grooves 301b for forming a bayonet join and with a hemispherical socket 311b as the proximal end thereof. Passage 261 preferably has a groove 271a for receiving a corresponding ridge on the surface of hollow plug 271, the ridge and groove serving to hold said plug in place.

Container 121 is closed by stopper 101 having a flange 111 which seats on the open end of container 121. Stopper 101 has an axial passage therethrough traversed by tube 141 which fits within stopper 101 sufficiently tightly to prevent the entry of air between tube 141 and the axial passage in stopper 101, but not so tightly as to prevent axial or rotational movement of tube 141 in stopper 101.

Tube 141 is closed at its proximal end, preferably by a frustoconical section 151 cemented or otherwise joined to the end of tube 141. Frustoconical section 151 performs the double function of sealing the proximal end of tube 141 and simultaneously limiting the axial excursion of container 121 in the proximal direction by seating in a mating socket 151a in stopper 101.

Tube 141 has a lateral opening 161 therein located a short distance away from the sealed end of tube 141. As shown in FIG. 2, opening 161 lies within the passage through stopper 101, thus effectively sealing container 121 against the entry of air when container 121 is evacuated. In a preferred form the axial passage through stopper 101 is threaded from the exterior portion thereof inwardly to a distance short of that at which opening 161 will be positioned when section 151 is seated in the mating portion 151a of stopper 101. As is obvious, tube 141 must be correspondingly threaded.

FIG. 2 shows the container portion of the device about to be joined to the support portion. The join is effected by inserting the distal tip 191 of tube 141 in aperture or passage 291. Tip portion 401 of tube 141 and aperture 291 are shaped so that they mate closely preventing leakage of air therebetween. As tip 191 is inserted into aperture 291, upper portion 271' of plug 271 is displaced downwardly, thereby establishing a continuous passage through opening 291 from the tip of cannula 23 to the interior of tube 141. This is shown in FIG. 3 in which the upper wall 271' of flexible plug 271 is depressed by tip 191. The appearance of the support portion of the device after insertion of tip 191 into aperture 291 is shown in section in FIGS. 3, 4 and 6.

When it is desired to take a blood sample, container 121 is carefully rotated in the direction shown by the arrow in FIG. 4 until opening 161 just clears the proximal end of cylindrical passage 101a in stopper 101. Axial movement of the container 121 in the proximal direction results from the fact that tube 141 has threads 131 thereon which mate with threaded portion 131' of stopper 101. It will be noted that stopper 101 has an unthreaded portion at its proximal end, thereby ensuring a tight seal when opening 161 is within the cylindrical passage 101a in stopper 101.

If blood does not flow virtually immediately through opening 161 into container 121, container 121 is rotated in the opposite direction to bring opening 161 within passage 101a and seat frustocone 151 in stopper 101, thereby avoiding the application of the full difference in pressure to the tissue in which the cannula must be imbedded. In this way, extravasation of blood and consequent hematoma are avoided if the cannula tip 24 is improperly positioned. Should such be the case, the cannula 23 can then be withdrawn and properly reinserted so that the tip 24 lies within a blood vessel. The container 121 is then rotated again as shown in FIG. 4 for starting the flow of blood. Assuming that blood flows through opening 161, rotation of container 121 is continued until stopper 101 hits periphery 321 of support section 221. It is kept in this position until the required amount of blood is drawn or until the container is filled.

Tube 141 has two sections 141a and 141b making an angle with each other. To join the support and container portions of the device, tip 191 of tube 141 is inserted into socket 291 in support portion 221. Lugs 301a enter grooves 301b in support portion 221 and a twist of the container portion 351 effects a bayonet lock between lugs 301a and grooves 301b. Also, socket 291 has a spherical portion 311b which mates with a corresponding spherical portion 311a on tube 141, effecting a tight seal between the support and container portions. Preferably, tip portion 401 also fits tightly within passage 291 to effect a seal also.

The manner in which lugs 301a seat in grooves 301b is shown more clearly in FIGS. 5 and 6. Also, the way in which liquid can pass from the cannula into the container 121 can be seen in FIGS. 4 and 6.

Once the container is filled, tip 191 of tube 141 is removed from socket 291 and flexible wall of plug 271 springs back into place to seal off passage 261 in support section 221. The process can be repeated as many times as desired using a fresh vessel each time for extracting a sample.

The spacing between the proximal periphery 321 of support section 221 and face 381 of stopper 101 when opening 161 is closed, closing being effected by moving container 351 proximally to its limit, is such that region 371 will just clear corner 361 of support portion 221. As a result, the container portion cannot be removed for transfer of same without tightly closing same prior to removal of said container portion from the support portion. Moreover, where the grooves 301b are spiral so that the seal between surfaces 311a and 311b is broken during partial displacement of the container portion, the seal between surface 401 and socket 291 is maintained. Such partial displacement can occur if an attempt is made to remove the container portion 351 without closing the valve therein completely.

Although the bayonet grooves 301b are shown as being spiral, they may also be circular, in which case the seal between surfaces 311a and 311b is maintained even during an attempt to remove the container portion in incompletely closed condition.

If desired a soluble drug can be injected without pain to the patient by filling with the drug a regular syringe assembled to a small caliber needle and piercing stopper 271 through aperture 281 by means of the syringe's pointed needle. The drug is then injected inside passage 261 and through this goes to cannula 23, aperture 24 and finally the patient's blood vessel given that aperture 291 remains sealed. A new container portion might be assembled to the in situ support section 221 to draw more blood or else cannula 23 might be removed from the blood vessel and then discarded. The filled container portion is shipped to a suitable biochemical laboratory where valve 161 is first opened after which the stopper 101 can readily be removed, the tests performed, and the unit discarded.

Since opening 291' is closed off each time a container portion is removed, blood tends neither to continue to flow out through passage 261 nor to withdraw into the blood vessel.

It will thus be seen that the objects set forth above, among those made apparent from the preceding description, are efficiently attained and, since certain changes may be made in the above article without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An improvement in a blood-taking device for taking blood from a blood vessel, wherein said improvement comprises a support portion and a container portion, said support portion comprising a cannula having a sharp distal end and a proximal end, said support portion having a passage therethrough, the distal end of said passage tightly receiving the proximal end of said cannula, first valve means seated in the proximal end of said passage for closing same, said support portion having an aperture therein connecting with said passage, said first valve means normally closing the connection between said aperture and said passage, said container portion comprising an evacuable container having a mouth, a stopper in said mouth, and tube means having a proximal end passing through said stopper and having a distal end removably connected with said aperture in said support portion to form a tight connection between said tube means and said support portion at said aperture therein, said distal end of said tube means serving for opening said first valve means and thereby connecting said aperture with said passage when said tube means is connected to said support portion, said stopper being affixed to said container for movement therewith relative to said tube means and fitting sufficiently tightly to said mouth to prevent flow of air therebetween.

2. The improvement as defined in claim 1, wherein said first valve means comprises a flexible plug seated in and closing said proximal passage end, said plug extending across and completely blocking said aperture when said tube means is not connected to said support section.

3. The improvement as defined in claim 1, wherein the distal end of said tube means is adapted to fit tightly within said aperture and form a seal therewith.

4. The improvement as defined in claim 1, wherein said stopper has an axial channel therethrough, and said tube means fits within said channel sufficiently tightly to prevent flow of fluid between said tube means and said channel, said tube means having an expanded portion at the proximal end thereof closing said proximal end and having an opening in the side wall thereof proximate said expanded portion, said container being axially movable relative to the proximal end of said tube means by an amount sufficient so that said opening in said tube means in a first state may be within said container thereby establishing connection between said tube means and said container, or in a second state within said channel in said stopper thereby sealing said container against possible entry of air or liquid thereinto from said tube means, said expanded section serving as a stop to limit the excursion of said container in the proximal direction.

5. The improvement as defined in claim 4, wherein he distal end of said channel in said stopper and the exterior of the proximal end of said tube means are correspondingly threaded so that gradual making and breaking of connection between said tube means and said container may be effected by rotation of said container about said tube.

6. The improvement as defined in claim 4, wherein the proximal end of said tube means and the proximal end of said stopper channel are of mating shapes whereby seating of said proximal end of said tube means in said mating channel effects a tight seal therebetween.

7. The improvement as defned in claim 6, wherein said mating shapes are frustoconical.

8. The improvement as defined in claim 1, wherein said first valve means is a hollow plug of material through which a hypodermic needle may be passed for injecting fluid into a patient once a puncture in the surface of a patient has been made for withdrawing blood.

9. The improvement as defined in claim 4, wherein the axial excursion of said container relative to said tube means is limited in the proximal direction by said proximal end of said tube means making contact with said stopper and in the distal direction by said stopper making contact with said support portion.

10. The improvement as defined in claim 9, wherein the spacing between said support portion and said stopper is such as to permit separating of said container portion from said support portion only when said container is at the position of maximum separation from said support portion, this position corresponding to limitation of excursion of said container in the proximal direction, thereby ensuring that said second valve means is closed.

* * * * *